United States Patent [19]

Steingraber, Jr.

[11] Patent Number: 5,259,503
[45] Date of Patent: Nov. 9, 1993

[54] DISPOSABLE CONTAINER FOR SEPTIC OBJECTS

[76] Inventor: William J. Steingraber, Jr., 638 Washington St., Reading, Pa. 19601

[21] Appl. No.: 961,624
[22] Filed: Oct. 16, 1992
[51] Int. Cl.⁵ .............................................. B65D 43/14
[52] U.S. Cl. ..................................... 206/440; 220/612
[58] Field of Search .............................. 206/438–440, 206/461; 220/359, 612, 613

[56] References Cited

U.S. PATENT DOCUMENTS

| | | | |
|---|---|---|---|
| 68,319 | 8/1867 | Spencer . | |
| 2,500,549 | 3/1950 | Ketay et al. . | |
| 3,135,455 | 6/1964 | Santangelo | 206/438 |
| 3,189,702 | 6/1965 | Wall et al. | 206/440 |
| 3,296,802 | 1/1967 | Williams | 220/613 |
| 3,385,470 | 5/1968 | Dorosz et al. | 220/613 |
| 3,938,659 | 2/1976 | Wardwell | 206/440 |
| 4,182,336 | 1/1980 | Black . | |
| 4,664,259 | 5/1987 | Landis . | |
| 4,721,679 | 1/1988 | Yiu et al. . | |
| 4,735,316 | 4/1988 | Froidh et al. . | |
| 4,759,463 | 7/1988 | Mazoin | 220/359 |
| 4,846,828 | 7/1989 | Mendelsohn . | |
| 4,857,066 | 8/1989 | Allison . | |
| 4,946,038 | 8/1990 | Eaton . | |
| 4,989,733 | 2/1991 | Patry . | |
| 5,012,928 | 5/1991 | Profitt . | |
| 5,031,768 | 7/1987 | Fischer . | |
| 5,046,613 | 9/1991 | Baudry et al. . | |
| 5,133,457 | 7/1992 | Kadel . | |

FOREIGN PATENT DOCUMENTS

| | | | |
|---|---|---|---|
| 0675537 | 12/1963 | Canada | 220/612 |
| 3833281 | 3/1990 | Fed. Rep. of Germany | 206/438 |

*Primary Examiner*—Jimmy G. Foster
*Attorney, Agent, or Firm*—Irvin A. Lavine

[57] ABSTRACT

A container of combustible material is provided for disposal, in an ecologically satisfactory manner, of septic bodies, such as a used sanitary napkin, tampon or bandage. The container comprises two parts, with at least one part providing an open, obstructed space for the reception of the septic body. One of the parts of the container has an adhesive body which completely encircles it. The adhesive body is initially protected by a removable cover. When the parts are assembled, so that both parts are in contact with the adhesive, the adhesive provides a continuous bonding of the parts of the container to hermetically seal the container. The adhesive is sufficiently strong to prevent manual separation of the parts. The container may be used to ship and store an aseptic body, prior to use, and then be used for the reception, sealing and disposal of the same or a similar body which has become septic.

23 Claims, 2 Drawing Sheets

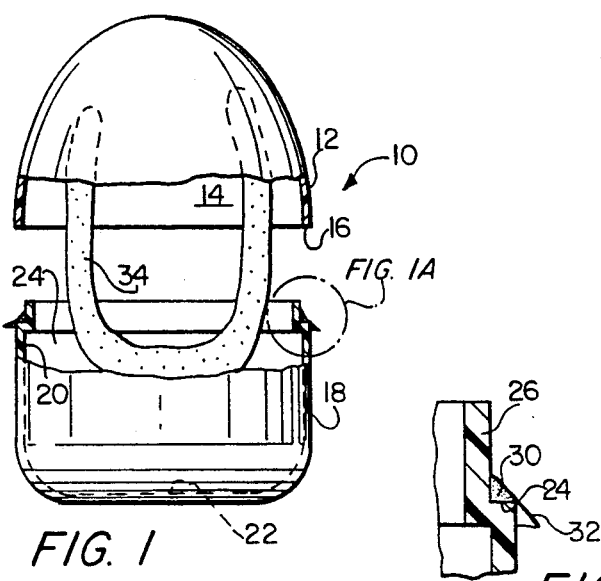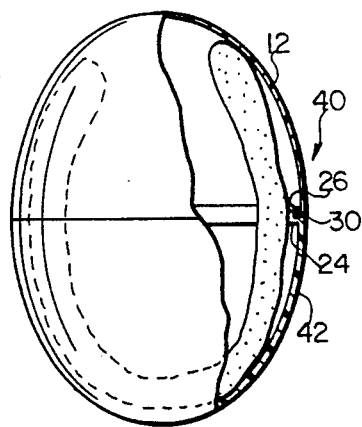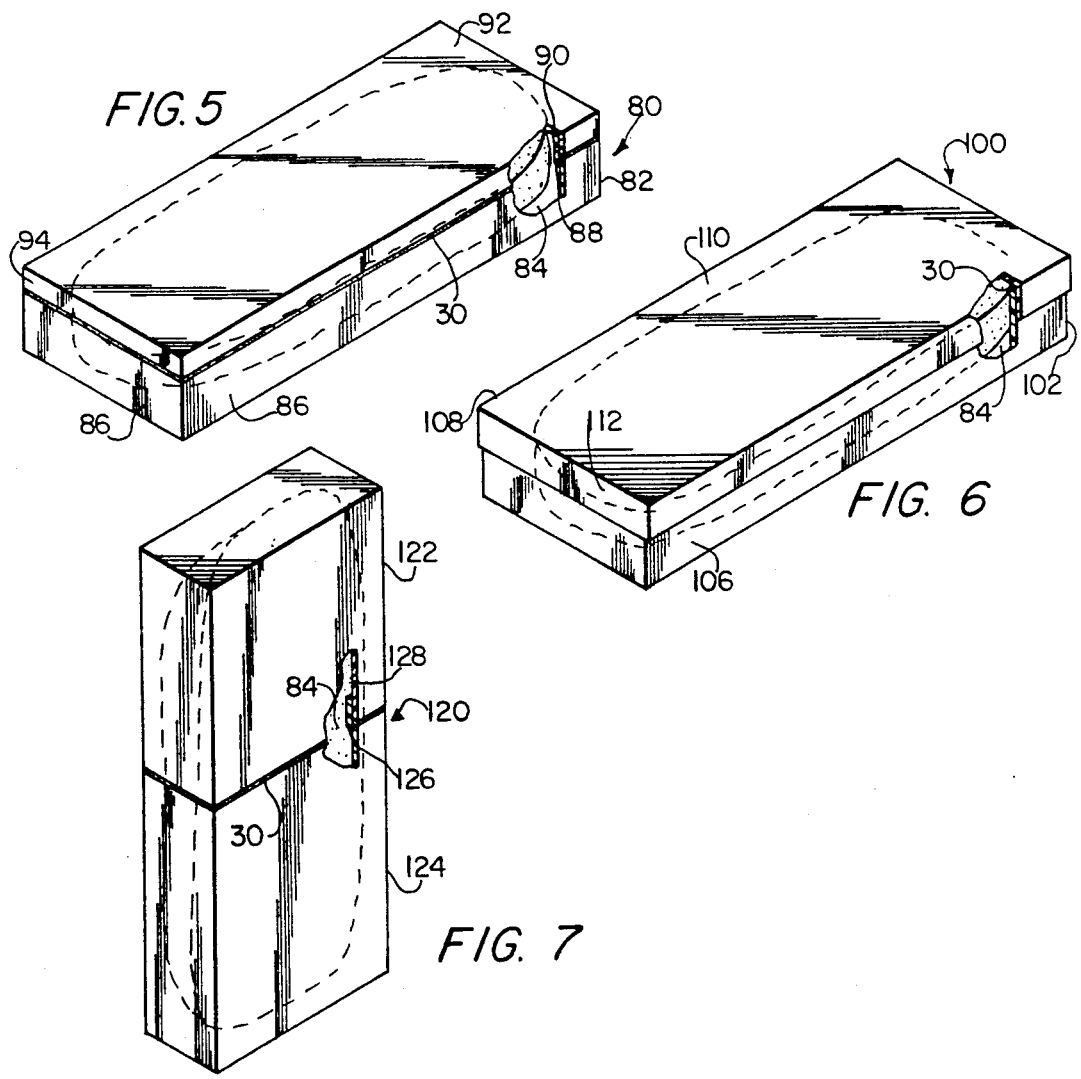

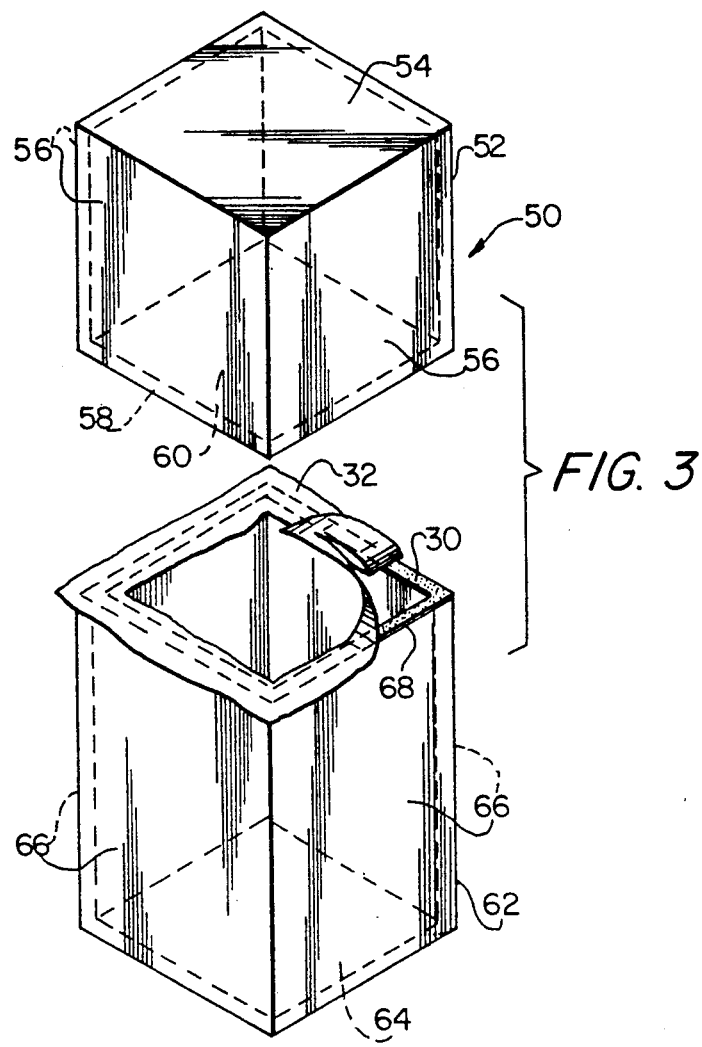
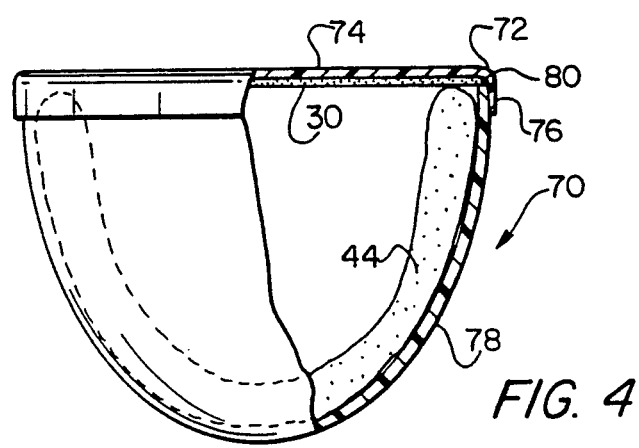

DISPOSABLE CONTAINER FOR SEPTIC OBJECTS

BACKGROUND OF THE INVENTION

The present invention is directed to a container, and more particularly to a container which may be used for the disposal of infectious septic articles to prevent contamination of the environment or the transmittal of disease.

FIELD OF THE INVENTION

It is known that the disposal of various kinds of waste must be accomplished in a manner to avoid a number of hazards, including hazards to the environment, that is, to the land, to air, and to bodies of water, including rivers, lakes, and the oceans. In recent years, the disposal of waste which is identified as being hazardous to persons or to the environment has increased, and expanded, and the disposal of chemical and medical wastes has received greater attention. Regulations have been and are being issued by Governmental bodies with regard to the disposal of ever increasing categories of waste.

Among the articles disposed of as waste are sanitary napkins and tampons. These have traditionally been disposed of with waste from bathrooms, such as soiled paper towels, or by being flushed down the toilet. Formerly, it was not considered that the disposal of these articles in this manner created an environmental hazard or was otherwise undesirable.

More recently, it has been recognized that the disposal of sanitary napkins might result in the transmission of the HIV virus, the cause of the AIDS disease. Mendelssohn U.S. Pat. No. 4,846,828 provides a recognition of this problem; the resulting danger has greatly increased due to the spread of AIDS to a greater number of women in the population. The proposal of this patent is to have a sanitary napkin and a disposal means connected to it, so that after the sanitary napkin has been used, the attached or "self-contained" disposal means, a wrapping, is folded over the soiled portion of the sanitary napkin. The disposal means or wrapping is intended to completely encloses the soiled napkin.

There are a number of disadvantages of the product of the noted patent. The wrapping or "package" itself adds to the bulk of the product when worn, and consequently to the discomfort of the wearer. Moreover, the structure of this patent requires that it be properly manipulated in order to provide the seal. The cover or wrapping which is attached to the sanitary napkin must be very carefully handled in order to achieve a sealed wrapping of the sanitary napkin. The construction requires the adhering of an adhesive tape to a surface of the used sanitary napkin, but this can be difficult or impossible since the used sanitary napkin often contains a very substantial amount of liquid, or is otherwise made moist. The user has to grasp and move separate sections of the wrapping so as to encompass the soiled sanitary napkin while holding the sanitary napkin. Further, there is not provided a hermetic sealing by the structure disclosed in this patent.

Froidh et al U.S. Pat. No. 4,735,316 discloses a sanitary napkin and a container for it in the form of a bag, the bag being usable as a disposal container after use of the sanitary napkin; the bag is neither sealed when closed with the used sanitary napkin, nor hermetically sealed.

Black U.S. Pat. No. 4,182,336 provides a sanitary napkin having a sack-like container attached to it, the container being made of moisture-proof material, and the used sanitary napkin is placed in the bag, and the bag is then closed by manipulation of a flap which is secured in the closed position by adhesive.

Allison U.S. Pat. No. 4,857,066 also provides a bag which is attached to a sanitary napkin, and which is used for disposal of the sanitary napkin after use, the structure including adhesive spots of pressure sensitive adhesive, in spaced relationship, to secure a flap of the bag in closed position; this construction does not provide a sealed or a hermetically sealed bag.

Kadel U.S. Pat. No. 5,133,457 provides a tampon applicator and container, which provides for disposal of a tampon applicator, but not of a tampon.

SUMMARY OF THE INVENTION

There is provided a container for disposing of such septic potentially infectious articles as sanitary napkins, tampons and other bandages, i.e. an absorbent body to absorb body fluid. The container is made of combustible material and comprises two parts, such as a top and a bottom. The two parts, when assembled, provide an unobstructed enclosed space for readily receiving a bandage such as a sanitary napkin or tampon. One of the parts has a peripheral edge adjacent an opening into the enclosed space, or into a part of the enclosed space. One of the parts is provided with an adhesive body which extends completely about a peripheral edge, and the two parts may be initially separate, assembled, or nested, there being a removable protective covering on the adhesive so as to prevent contact of either the other part of the container or any other object with the adhesive. Upon removal of the protective cover, the used bandage such as a sanitary napkin or tampon may be readily placed into one part of the container, the protective cover of the adhesive then being removed, and the other part moved to close the container and, by engaging the adhesive, being bonded to the first part of the container. The adhesive is pressure sensitive, bonding upon contact, and providing a hermetic seal: the adhesive is sufficiently strong to prevent manual separation of the parts.

Among the objects of the present invention are to provide a disposable container for septic, infectious material which will prevent contamination.

Another object of the present invention is to provide such a container which may be readily disposed of, together with its contents, by suitable, conventional and inexpensive methods, such as burning.

A further object of the present invention is to provide a container for the disposal of such articles which may be readily manufactured and shipped, and which is of low cost.

Still another object of the present invention is the provision of a container for the disposal of such articles which may be readily and easily used, without undue manipulation, and which will enable the hermetic and strong sealing of the container after placement of an article therein.

Other objects and many of the attendant advantages of the present invention will be readily understood from the accompanying specification, claims and drawings.

BRIEF DESCRIPTION OF THE DRAWINGS

FIG. 1 is an exploded view, with parts in section, of a container and a sanitary napkin in accordance with the present invention.

FIG. 1a is an enlarged view of the structure in the circle designated FIG. 1a of FIG. 1.

FIG. 2 is an elevational view, with parts in section, of a sealed container and a sanitary napkin therein, in accordance with the present invention.

FIG. 3 is a perspective exploded view of another embodiment of a container in accordance with the present invention.

FIG. 4 is an elevational view, with parts in section, of a further embodiment of a container and sanitary napkin, in accordance with the present invention.

FIG. 5 is a perspective view, with parts removed and in section, of a another embodiment of a container and sanitary napkin in accordance with the present invention.

FIG. 6 is a perspective view, with parts removed and in section, of a further embodiment of a container and sanitary napkin in accordance with the present invention.

FIG. 7 is a perspective view, with parts removed and in section, of still another embodiment of a container and sanitary napkin in accordance with the present invention.

DESCRIPTION OF THE PREFERRED EMBODIMENTS

Referring now to the drawings, wherein like or corresponding reference numerals are used for like or corresponding parts throughout are used, there is shown in FIG. 1 a container generally designated 10 and comprising a first part 12 which is generally in the form of the end portion of a poultry egg, extending to a large diameter circumference of such poultry egg. The part 12 encompasses an unobstructed space 14 extending inwardly from an edge 16 thereof. The second part 18 comprises a generally cylindrical wall 20 and a bottom 22 joined to it, the wall 20 having at its upper end, as shown in FIG. 1a, a shoulder 24 and, interiorly thereof, an upstanding peripherally extending ridge 26. On the shoulder 24 is a body of adhesive 30, the adhesive 30 extending entirely about the part 18, and is continuous and unbroken. The adhesive body 30 is provided with a protective covering 32 of paper, or the like, which may be readily removed from the adhesive body 30, but which protects it from engagement with another object, such as the part 12, until it is removed. The part 18 provides an open space 28 in it, which is unobstructed, and which may readily receive a part of a sanitary napkin or other absorbent body.

There is shown in FIG. 1, within the container 10, occupying the spaces 14 and 34, an absorbent body 34, i.e., a bandage which is unused, i.e. aseptic. The absorbent body 34 may have a disposable cover (not shown) and is specifically a new, ready-for-use sanitary napkin. Alternatively, the bandage 34 may be a tampon, or other product of material, shape and size to absorb body fluids.

When assembled, the body 34 may be placed in the part 18, and with the covering 32 in place, the part 12 is associated with the part 18, guidance for such association being provided by the upstanding ridge 26. Thus, there will be provided a container 10 with an unused aseptic, and ready-for-use absorbent body 34. The part 12 will not be bonded to the part 18, since the adhesive 30 will not be in engagement with the part 12.

The container 10 with the unused and aseptic absorbent body 34 therein may be placed at convenient locations, such as in rest rooms, or medical facilities, and may be carried by a person. The container 10 with the body 34 therein is therefore readily available for use, since there will be no impediment to the disassociation of part 12 from part 18, thereby providing ready access to the sanitary body 34.

After the container 10 has been separated and the new sanitary absorbent body 34 has been removed, the parts 12 and 18 are retained for re-use, to receive a used, septic and possibly infectious absorbent body, which may or may not be the absorbent body which was removed from the container 10. When a used absorbent body is to be disposed of, it is placed within one or another of the parts 12 and 18, the protective cover 32 is removed, and the parts 12 and 18 are associated together so that the adhesive 30 is in contact with both of the parts 12 and 18.

The adhesive 30 provides a substantially permanent bond between these parts and is of sufficient strength to prevent the manual separation of the parts 12 and 14. The adhesive 30 also provides a hermetic seal between the container parts 12 and 42. Among the adhesives which are suitable is Adhesive 4693 of 3M Company, St. Paul, Minnesota.

Container 10, and each of the containers herein disclosed, is made of material which is readily combustible, so that the container and the used and possibly infectious absorbent body within it may be disposed of by burning, in accordance with established procedures and regulations. The material of which the container is made includes combustible plastic, as well as other materials such as those which are paper-based.

In FIG. 2, there is shown an egg-shaped container 40 comprising an upper part 12, and a lower part 42 having the shape of a part of a poultry egg. The part 42 will be seen to have a shoulder 24 and a ridge 26, with an adhesive body 30 on the shoulder 24. The lower portion of the part 12 engages the adhesive 30, and the adhesive 30 thereby serves to bond the parts 12 and 42.

The space within the container 40 is unobstructed, so that the space readily contains a used absorbent body 44, such as a used sanitary napkin, tampon or bandage which may contain body fluids. Since such body fluids may be infectious, and therefore the body 44 may be infectious, the container 40, including the adhesive 30, seals the used absorbent body 44 therewithin and is not hazardous.

In FIG. 3, there is shown another embodiment of a container in accordance with the present invention. The container 50 comprises a first part 52 having a top 54 of square configuration, and depending walls 56, the walls terminating in a peripherally extending edge 58 located at the bottoms thereof, and surrounding an opening into the unobstructed space 60 within the part 52. A similarly shaped second or bottom part 62 has a bottom 64 which is congruent with the top 54, and has walls 66 extending upwardly therefrom and which are in alignment with the walls 56. On the upper edge 68 of the walls 66 is a body of adhesive 30, shown partly covered with a protective strip 32. The total height of the container 50 is substantially equal to the height of a used septic absorbent body, such as a sanitary napkin (not shown). As will be understood, the protective strip 32 will have been removed, to expose the adhesive 30, so that the parts 52 and 62, with their substantially unobstructed spaces, may be joined at their edges to provide a butt joint. There is provided a disposable container 50 with the septic body therein, and which is both hermetically sealed and incapable of being separated by manual force.

There is shown in FIG. 4 a further embodiment of the present invention, there being provided a container 70 having a first part 72 having a top 74 in the form of a flat disc, which may be provided with a depending annular flange 76. There is also provided a second part 78 shaped generally like the part 42 of FIG. 2, and having an upper edge 80 on which there is an adhesive body 30 which bonds to the underside of the top 74. Within the body 78 there is a used, septic absorbent body 44, which may be a sanitary napkin.

FIG. 5 is a perspective view of a container 80 which is of generally elongate parallelepiped shape and size so as to closely encompass a sanitary napkin 84. Container 80 comprises a tray-like bottom part 82 having a length and width substantially equal to the length and width of the sanitary napkin 84 and having a height provided by the walls 86 which is somewhat less than the thickness of the sanitary napkin 84. The walls 86 include a shoulder 88 and an upstanding ridge 90; a body of adhesive 30 is on the shoulder 88. The top part 92 is of substantially the same length and width as the bottom part 82 and has depending walls 94 which have internal dimensions slightly greater than the ridge 90, so as to be guided thereby. The bottom edges of the walls 94 engage the adhesive 30, so that the container with the used septic sanitary napkin 84 is hermetically sealed, and the container 80 may not be opened by manual force.

In FIG. 6, there is a generally elongate parallelepiped container 100, having a first, bottom part 102 of the same shape and size as the bottom part 82, but having a height of the walls 106 thereof substantially equal to the thickness of a used septic sanitary napkin 84. The top edge of the walls 86 is provided with a body of adhesive 30, and the second or top part 108 of the container 100 has a rectangular top 110, the bottom surface of which engages the adhesive 30, and the depending walls 112 of which telescope over a portion of the walls 106 of the first or bottom part 102.

FIG. 7 discloses a container 120 in accordance with the present invention comprising a first part 122 and a second part 124, each of which has a width substantially equal to the width of a sanitary napkin 84 and a depth substantially equal to the thickness of the sanitary napkin 84. The total height of the container 120, comprised of the parts 122 and 124, is substantially equal to the length of the sanitary napkin 84; each of the parts 122 and 124 has a height which is less than the length of sanitary napkin 84. The part 124 will be seen to have a shoulder 126 with adhesive 30 thereon, and an upstanding ridge 128. Ridge 128 has an exterior size and shape slightly smaller than the interior size and shape of the part 122, and thereby serves to guide the part 122 into engagement with the adhesive 30 on the shoulder 126.

There has been provided a container which may be readily used for the disposal of septic, potentially infectious bodies, such as absorbent bodies that may have body fluids in them. Such absorbent bodies or bandages include sanitary napkins, tampons, and bandages. The container herein provided has a substantially unobstructed space for receiving the septic body and is made of separable parts which are bonded together by an adhesive which provides both a hermetic seal and a bonding of such strength as to prevent manual disassembly.

The insertion of a septic body, such as a used sanitary napkin, may be readily accomplished, requiring no complicated manipulation. When put in the container or container part, and after removal of the protective cover from the adhesive, a hermetically sealed container, incapable of being manually opened, results. The sealed container may be disposed of in an ecologically acceptable manner, such as by incineration, due to the fact that the container is made of combustible material.

The herein disclosed container may be used to ship and/or store an aseptic, unused sanitary napkin or other absorbent body. Such an aseptic body, which can be properly packaged to maintain its aseptic condition, may be placed in the container with the parts of the container joined, but one part being separated from contact with the adhesive by a protective layer on the adhesive, so that the parts of the container are readily separable.

The herein disclosed container is readily usable, both to extract a body from the container and to place a body within a container, and to provide a hermetic sealing of the container with the aseptic within it.

The claims and specification describe the invention presented, and the terms that are employed in the claims draw their meaning from the use of such terms in the specification. Some terms employed in the prior art may be broader in meaning than specifically employed herein. Whenever there is a question between the broader definition of such term as used in the prior art and the more specific use of the term herein, the more specific meaning is meant.

What is claimed is:

1. A container for the disposal of septic articles, said container comprising:
   a first part and a second part defining an enclosed space free of obstructions, at least one said part having a peripheral edge,
   an adhesive body on said first part and extending about the peripheral edge thereof,
   said adhesive providing a substantially permanent bond between said parts of strength sufficient to resist manual separation of said parts,
   said adhesive providing a hermetic seal between container parts,
   said container parts being made of material which is combustible, and
   a used absorbent body therein.

2. The container of claim 1, said used absorbent body being a sanitary napkin.

3. The container of claim 1, wherein said first part comprises a peripheral shoulder and an upstanding peripheral ridge at the opening into the space in said first part, said adhesive being on said shoulder.

4. The container of claim 3, wherein said second part has an enclosed space with an opening thereinto, said upstanding ridge having external dimensions slightly less than the internal dimensions of said second part at the opening thereof, said ridge thereby providing a guide for the engagement of said second part and said first part of said container.

5. The container of claim 1, at least one said part having the shape of the end portion of a poultry egg.

6. The container of claim 5, the second part comprising an annular wall, and a bottom.

7. The container of claim 5, wherein both said parts are the shape of a part of a poultry egg.

8. The container of claim 5, and wherein said second part is generally flat, and extends across the edge of said first part.

9. The container of claim 1, wherein said parts of said container, when joined, provide a container generally having the shape of a poultry egg.

10. The container of claim 1, wherein said one part has a bottom having the shape of a multi-sided geometric figure, and upstanding walls substantially perpendicular to said bottom, said second part having a top substantially congruent to said bottom and having depending walls, said adhesive bonding the edges of said walls of said first part and the edges of said walls of said second part.

11. The container of claim 10, wherein said edges of said walls of said parts and said adhesive provide a butt joint.

12. The container of claim 10, wherein said bottom and said top are of square configuration.

13. The container of claim 2, said container being of generally elongate parallelepiped shape and size for closely encompassing said sanitary napkin.

14. The container of claim 13, said one part providing a bottom having a length and a width substantially equal to the length and width of said sanitary napkin contained therein, and having a height less than the thickness of said sanitary napkin, and said second part being of generally the same shape as said first part, said sanitary napkin having a thickness greater than the height of said first part.

15. The container of claim 13, said first part having a length and width substantially equal to the length and width of said sanitary napkin contained therein, and having a height substantially equal to the thickness of said sanitary napkin contained therein, said second part comprising at least a planar top, said adhesive engaging the under side of the top of said second part.

16. The container of claim 15, said second part having depending walls telescoping over the walls of said first part.

17. The container of claim 13, said first and second parts having a width substantially equal to the width of the sanitary napkin contained therein and a depth substantially equal to the thickness of the sanitary napkin contained therein, said first and second parts together having a height substantially equal to the length of the sanitary napkin contained therein, each of said first and second parts having a length less than the length of said sanitary napkin contained therein.

18. A container for the disposal of a septic article, such as an absorbent body intended to receive and absorb a body fluid, said container comprising:
   first and second parts which may be assembled to define an enclosed space which is substantially free of obstructions and which space is sufficient in volume and dimensions to receive at least one such absorbent body when said parts are assembled,
   at least one of said parts having a peripheral edge defining an opening thereinto,
   an adhesive body on said one part and assembled about the peripheral edge of said one part,
   a removable protective covering on said adhesive body to prevent contact of said adhesive with the other part of said container,
   said adhesive being a material capable of providing a substantially permanent bond between said parts, when joined, of a strength sufficient to prevent manual separation of said parts, and said adhesive body providing a hermetic seal between said container parts,
   said container parts being made of material which is combustible.

19. The container of claim 18, and further comprising an unused absorbent body in said container.

20. The container of claim 18, wherein said part comprises a peripheral shoulder and an upstanding peripheral ridge at the opening into the space in said first part, said adhesive being on said shoulder.

21. The container of claim 18, at least one said part having the shape of the end portion of a poultry egg.

22. The container of claim 18, in combination therewith, wherein said one part has a bottom having the shape of a multi-sided geometric figure, and upstanding walls substantially perpendicular to said bottom, said second part having a top substantially congruent to said bottom and having depending walls, said adhesive bonding the edges of said walls of said first part and the edges of the said walls of said second part.

23. The container of claim 18, said container being of generally elongate parallelepiped shape and size for closely encompassing a sanitary napkin.

* * * * *